US012624058B2

(12) United States Patent
Mckenna

(10) Patent No.: US 12,624,058 B2
(45) Date of Patent: May 12, 2026

(54) PROMOIETY STRATEGY TO ENHANCE DRUG ACTIVITY

(71) Applicant: UNIVERSITY OF SOUTHERN CALIFORNIA, Los Angeles, CA (US)

(72) Inventor: Charles E. Mckenna, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 397 days.

(21) Appl. No.: 18/021,753

(22) PCT Filed: Aug. 18, 2021

(86) PCT No.: PCT/US2021/046486
§ 371 (c)(1),
(2) Date: Feb. 16, 2023

(87) PCT Pub. No.: WO2022/040301
PCT Pub. Date: Feb. 24, 2022

(65) Prior Publication Data
US 2023/0322823 A1      Oct. 12, 2023

Related U.S. Application Data

(60) Provisional application No. 63/067,204, filed on Aug. 18, 2020.

(51) Int. Cl.
| | |
|---|---|
| C07H 7/06 | (2006.01) |
| C07F 9/6512 | (2006.01) |
| C07F 9/6561 | (2006.01) |

(52) U.S. Cl.
CPC .......... C07F 9/6561 (2013.01); C07F 9/6512 (2013.01); C07H 7/06 (2013.01)

(58) Field of Classification Search
None
See application file for complete search history.

(56) References Cited

U.S. PATENT DOCUMENTS

| | | | | |
|---|---|---|---|---|
| 8,940,313 B2 * | 1/2015 | McKenna | ............... | A61P 31/20 |
| | | | | 424/402 |
| 9,550,803 B2 * | 1/2017 | McKenna | ............... | C07H 19/10 |
| 2008/0274686 A1 | 11/2008 | Kupferberg et al. | | |
| 2009/0156545 A1 | 6/2009 | Hostetler et al. | | |
| 2009/0274686 A1 | 11/2009 | Or et al. | | |
| 2011/0263535 A1 | 10/2011 | Mckenna et al. | | |
| 2014/0100186 A1 | 4/2014 | McKenna et al. | | |

FOREIGN PATENT DOCUMENTS

| | | |
|---|---|---|
| WO | WO2005087788 A2 | 9/2005 |
| WO | 2008062206 A2 | 5/2008 |
| WO | 2018081785 A1 | 5/2018 |

OTHER PUBLICATIONS

Pochet et al., Nucleosides and Nucleotides, 1999, 18(4&5), pp. 1019-1020. (Year: 1999).*

Marty FM, Winston DJ, Rowley SD, Vance E, Papanicolaou GA, Mullane KM, Brundage TM, Robertson AT, Godkin S, Mommeja-Marin H, Boeckh M, Group CMXCS. CMX001 to prevent cytomegalovirus disease in hematopoietic-cell transplantation. N Engl J Med. 2013. 369(13):1227-1236. Epub Sep. 27, 2013. doi: 10.1056/NEJMoa1303688.

Lima WG, Brito JCM, Overhage J, Nizer W. The potential of drug repositioning as a short-term strategy for the control and treatment of COVID-19 (SARS-CoV-2): a systematic review. Arch Virol. 2020. 165(8):1729-1737. Epub Jun. 10, 2020. doi: 10.1007/s00705-020-04693-5.

Guy RK, DiPaola RS, Romanelli F, Dutch RE. Rapid repurposing of drugs for COVID-19. Science. 2020. 368 (6493):829-830. Epub May 10, 2020. doi: 10.1126/science.abb9332.

Mullard A. Hints of hope with remdesivir. Nat Rev Drug Discov. 2020. 19(6):373. Epub May 13, 2020. doi: 10.1038/d41573-020-00088-y.

Beigel JH, Tomashek KM, Dodd LE, Mehta AK, Zingman BS, Kalil AC, Hohmann E, Chu HY, Luetkemeyer A, Kline S, Lopez dCD, Finberg RW, Dierberg K, Tapson V, Hsieh L, Patterson TF, Paredes R, Sweeney DA, Short WR, Touloumi G, Lye DC, Ohmagari N, Oh M-D, Ruiz-Palacios GM, Benfield T, Fatkenheuer G, Kortepeter MG, Atmar RL, Creech CB, Lundgren J, Babiker AG, Pett S, Neaton JD, Burgess TH, Bonnett T, Green M, Makowski M, Osinusi A, Nayak S, Lane HC. Remdesivir for the Treatment of Covid-19—Preliminary Report. N Engl J Med. 2020.

Davies M, Osborne V, Lane S, Roy D, Dhanda S, Evans A, Shakir S. Remdesivir in Treatment of COVID-19: A Systematic Benefit-Risk Assessment. Drug Saf. 2020. 43(7):645-656. Epub May 30, 2020. doi: 10.1007/s40264-020-00952-1.

Jockusch S, Tao C, Li X, Anderson TK, Chien M, Kumar S, Russo JJ, Kirchdoerfer RN, Ju J. A library of nucleotide analogues terminate RNA synthesis catalyzed by polymerases of coronaviruses that cause SARS and COVID-19. Antiviral Res. 2020. 180:104857. Epub Jun. 21, 2020. doi: 10.1016/j.antiviral.2020.104857.

Peterson LW, McKenna CE. Prodrug approaches to improving the oral absorption of antiviral nucleotide analogues. Expert Opin Drug Deliv. 2009. 6(4):405-420. Epub Apr. 23, 2009. doi: 10.1517/17425240902824808.

Toth K, Spencer JF, Ying B, Tollefson AE, Hartline CB, Richard ET, Fan J, Lyu J, Kashemirov BA, Harteg C, Reyna D, Lipka E, Prichard MN, McKenna CE, Wold WSM. USC-087 protects Syrian hamsters against lethal challenge with human species C adenoviruses. Antiviral Res. 2018. 153:1-9. Epub Mar. 7, 2018. doi: 10.1016/j.antiviral. 2018.03.001.

(Continued)

*Primary Examiner* — Traviss C Mcintosh, III
(74) *Attorney, Agent, or Firm* — Brooks Kushman P.C.

(57) ABSTRACT

Various nucleoside phosphate and phosphonate analogues are provided for treatment of viral infections. Methods of preparing the analogues, pharmaceutical compositions containing the analogues, and methods of using the analogues as antiviral compounds, especially against adenoviruses, coronaviruses, and varicella zoster viruses, are also provided.

17 Claims, 9 Drawing Sheets

(56)        References Cited

OTHER PUBLICATIONS

Toth K, Spencer J, Tollefson AE, Ying B, Wold W, Reyna D, Ganesan S, Harteg C, Lipka E, Richard E, Lv J, Fan J, Kashemirov B, McKenna C, Prichard M. USC-087 and USC-505 Protect Immunosuppressed Syrian Hamsters Against Lethal Intravenous Challenge with Human Type 5 and 6 Adenoviruses. 29th International Conference on Antiviral Research (ICAR). 2016. La Jolla, CA.

Moffat J, Liu D, Coombs W, Reyna D, Ganesan S, Harteg C, Lipka E, Richard E, Lv J, Fan J, Kashemirov B, McKenna C, Prichard M. Tyrosine Ester Prodrug of Cidofovir is Effective Against VZV in Mice. 29th International Conference on Antiviral Research (ICAR). 2016. La Jolla, CA.

Grimm JB, Wilson KJ, Witter DJ. Suppression of racemization in the carbonylation of amino acid-derived aryl triflates. Tetrahedron Letters. 2007. 48(26):4509-4513. doi: 10.1016/j.tetlet.2007.04.145.

Kikuchi C, Nagaso H, Hiranuma T, Koyama M. Tetrahydrobenzindoles: selective antagonists of the 5-HT7 receptor. J Med Chem. 1999. 42(4):533-535. Epub Mar. 3, 1999. doi: 10.1021/jm980519u.

Zakharova VM, Serpi M, Krylov IS, Peterson LW, Breitenbach JM, Borysko KZ, Drach JC, Collins M, Hilfinger JM, Kashemirov BA, McKenna CE. Tyrosine-based 1-(S)-[3-hydroxy-2-(phosphonomethoxy)propyl]cytosine and -adenine ((S)-HPMPC and (S)-HPMPA) prodrugs: synthesis, stability, antiviral activity, and in vivo transport studies. J Med Chem. 2011. 54(16):5680-5693. Epub Aug. 5, 2011. doi: 10.1021/jm2001426.

Krylov IS, Zakharova VM, Serpi M, Haiges R, Kashemirov BA, Mckenna CE. Structure of cyclic nucleoside phosphonate ester prodrugs: an inquiry. J Org Chem. 2012. 77(1):684-689. Epub Dec. 1, 2011. doi: 10.1021/jo201735f.

McKenna CE, Schmidhuser J. Functional selectivity in phosphonate ester dealkylation with bromotrimethylsilane. Journal of the Chemical Society, Chemical Communications. 1979. (17):739-739. doi: 10.1039/c39790000739.

McKenna C, Higa M, Cheung N, McKenna M. The Facile Dealkylation of Phosphonic Acid Dialkyl Ester by Bromotrimethylsilane. Tetrahedron Lett. 1977. (2):155-158.

Marty FM, Winston DJ, Chemaly RF, Boeckh MJ, Mullane KM, Shore TB, Papanicolaou GA, Morrison ME, Brundage TM, Mommeja-Marin H. Brincidofovir for Prevention of Cytomegalovirus (CMV) after Allogeneic Hematopoietic Cell Transplantation (HCT) in CMV-Seropositive Patients: A Randomized, Double-Blind, Placebo-Controlled, Parallel-Group Phase 3 Trial. Biology of Blood and Marrow Transplantation. 2016. 22(3):S23-S23.

Lion T. Adenovirus infections in immunocompetent and immunocompromised patients. Clin Microbiol Rev. 2014. 27 (3):441-462. Epub Jul. 2, 2014. doi: 10.1128/CMR.00116-13.

Sandkovsky U, Vargas L, Florescu DF. Adenovirus: current epidemiology and emerging approaches to prevention and treatment. Curr Infect Dis Rep. 2014. 16(8):416. Epub Jun. 9, 2014. doi: 10.1007/s11908-014-0416-y.

Saquib R, Melton LB, Chandrakantan A, Rice KM, Spak CW, Saad RD, Fenves AZ, Barri YM. Disseminated adenovirus infection in renal transplant recipients: the role of cidofovir and intravenous immunoglobulin. Transpl Infect Dis. 2010. 12(1):77-83. Epub Sep. 19, 2009. doi: 10.1111/j.1399-3062.2009.00452.x.

Neofytos D, Ojha A, Mookerjee B, Wagner J, Filicko J, Ferber A, Dessain S, Grosso D, Brunner J, Flomenberg N, Flomenberg P. Treatment of adenovirus disease in stem cell transplant recipients with cidofovir. Biol Blood Marrow Transplant. 2007. 13(1):74-81. Epub Jan. 16, 2007. doi: 10.1016/j.bbmt.2006.08.040.

Wold WS, Toth K. New drug on the horizon for treating adenovirus. Expert Opin Pharmacother. 2015. 16 (14):2095-2099. Epub Sep. 4, 2015. doi: 10.1517/14656566.2015.1083975.

Cundy KC, Bidgood AM, Lynch G, Shaw JP, Griffin L, Lee WA. Pharmacokinetics, bioavailability, metabolism, and issue distribution of cidofovir (HPMPC) and cyclic HPMPC in rats. Drug Metab Dispos. 1996. 24(7):745-752. Epub Jul. 1, 1996.

Izzedine H, Launay-Vacher V, Deray G. Antiviral drug-induced nephrotoxicity. Am J Kidney Dis. 2005. 45(5):804-817. Epub Apr. 30, 2005. doi: 10.1053/j.ajkd.2005.02.010.

Williams-Aziz SL, Hartline CB, Harden EA, Daily SL, Prichard MN, Kushner NL, Beadle JR, Wan WB, Hostetler KY, Kern ER. Comparative activities of lipid esters of cidofovir and cyclic cidofovir against replication of herpesviruses in vitro. Antimicrob Agents Chemother. 2005. 49(9):3724-3733. Epub Aug. 30, 2005. doi: 10.1128/AAC.49.9.3724-3733.2005.

Hostetler KY. Alkoxyalkyl prodrugs of acyclic nucleoside phosphonates enhance oral antiviral activity and reduce toxicity: current state of the art. Antiviral Res. 2009. 82(2):A84-98. Epub May 9, 2009. doi: 10.1016/j.antiviral.2009.01.005.

De la Camara R. CMV in Hematopoietic Stem Cell Transplantation. Mediterr J Hematol Infect Dis. 2016. 8(1):e2016031. Epub Jul. 15, 2016. doi: 10.4084/MJHID.2016.031.

Lanier R, Trost L, Tippin T, Lampert B, Robertson A, Foster S, Rose M, Painter W, O'Mahony R, Almond M, Painter G. Development of CMX001 for the Treatment of Poxvirus Infections. Viruses. 2010. 2(12):2740-2762. Epub Apr. 19, 2011. doi: 10.3390/v2122740.

Hartline CB, Gustin KM, Wan WB, Ciesla SL, Beadle JR, Hostetler KY, Kern ER. Ether lipid-ester prodrugs of acyclic nucleoside phosphonates: activity against adenovirus replication in vitro. J Infect Dis. 2005. 191(3):396-399. Epub Jan. 6, 2005. doi: 10.1086/426831.

Tollefson AE, Spencer JF, Ying B, Buller RM, Wold WS, Toth K. Cidofovir and brincidofovir reduce the pathology caused by systemic infection with human type 5 adenovirus in immunosuppressed Syrian hamsters, while ribavirin is largely ineffective in this model. Antiviral Res. 2014. 112:38-46. Epub Dec. 3, 2014. doi: 10.1016/j.antiviral.2014.10.005.

Toth K, Spencer JF, Dhar D, Sagartz JE, Buller RM, Painter GR, Wold WS. Hexadecyloxypropyl-cidofovir, CMX001, prevents adenovirus-induced mortality in a permissive, immunosuppressed animal model. Proc Natl Acad Sci U S A. 2008. 105(20):7293-7297. Epub May 21, 2008. doi: 10.1073/pnas.0800200105.

Paolino K, Sande J, Perez E, Loechelt B, Jantausch B, Painter W, Anderson M, Tippin T, Lanier ER, Fry T, DeBiasi RL. Eradication of disseminated adenovirus infection in a pediatric hematopoietic stem cell transplantation recipient using the novel antiviral agent CMX001. J Clin Virol. 2011. 50(2):167-170. Epub Nov. 26, 2010. doi: 10.1016/j.icv.2010.10.016.

Grimley MS, Chemaly RF, Englund JA, Kurtzberg J, Chittick G, Brundage TM, Bae A, Morrison ME, Prasad VK. Brincidofovir for Asymptomatic Adenovirus Viremia in Pediatric and Adult Allogeneic Hematopoietic Cell Transplant Recipients: A Randomized Placebo-Controlled Phase II Trial. Biol Blood Marrow Transplant. 2017. 23(3):512-521. Epub Jan. 9, 2017. doi: 10.1016/j.bbmt.2016.12.621.

PCT Int'l Search Report dated Jan. 12, 2022 issued in connection with PCT/US2021/046486.

Pochet Sylvie et al., "Pyridoxal-Catalyzed Release of Nucleotides", Nucleosides and Nucleotides, vol. 18, No. 4-5, XP093252338, US, ISSN: 0732-8311 DOI: 10.1080/15257779908041635, Apr. 1, 1999, pp. 1019-1020.

EP Partial Search Report dated Mar. 11, 2025 for 21859049.5-1102/4199931 PCT/US2021046486, 14 pages.

EP Extended Search Report dated Jul. 21, 2025 for EP Application 21859049.5, 17 pgs.

* cited by examiner

CDV          HPMPA          BCV

FIG. 1

USC 505          USC 087

FIG. 2

ANP drug    Prodrug scaffold

Parent drugs:
B = natural or unnatural base,
e.g. cytosine in CDV/HPMPC
or adenine in HPMPA $R = H, C(O)NHR_2, R_2 = lipid-like$
$R_1 = H, lipid-like$
$X = CH_2Ph$ or $C_1$-$C_2$

FIG. 3

B = CDV or HPMPA

|  | R = | $R_1$ = | X = |
|---|---|---|---|
| Series A | H | $C_{12-18}$ alkyl $C_nCH=CHC_n$ alkyl | $CH_2Ph$ |
| Series B | H | $C_n$–O–$C_n$ $C_n$–S–$C_n$ | $CH_2Ph$ |
| Series C | $C_{8-18}C(O)$ | H | $CH_2Ph$ |
| Series D | Same as Series A–C | Same as Series A–C | $CH_2$ $CH_2CH_2$ $CHCH_3$ |

Ganciclovir

Cidofovir

Abacavir

Stavudine

Entecavir

FIG. 5

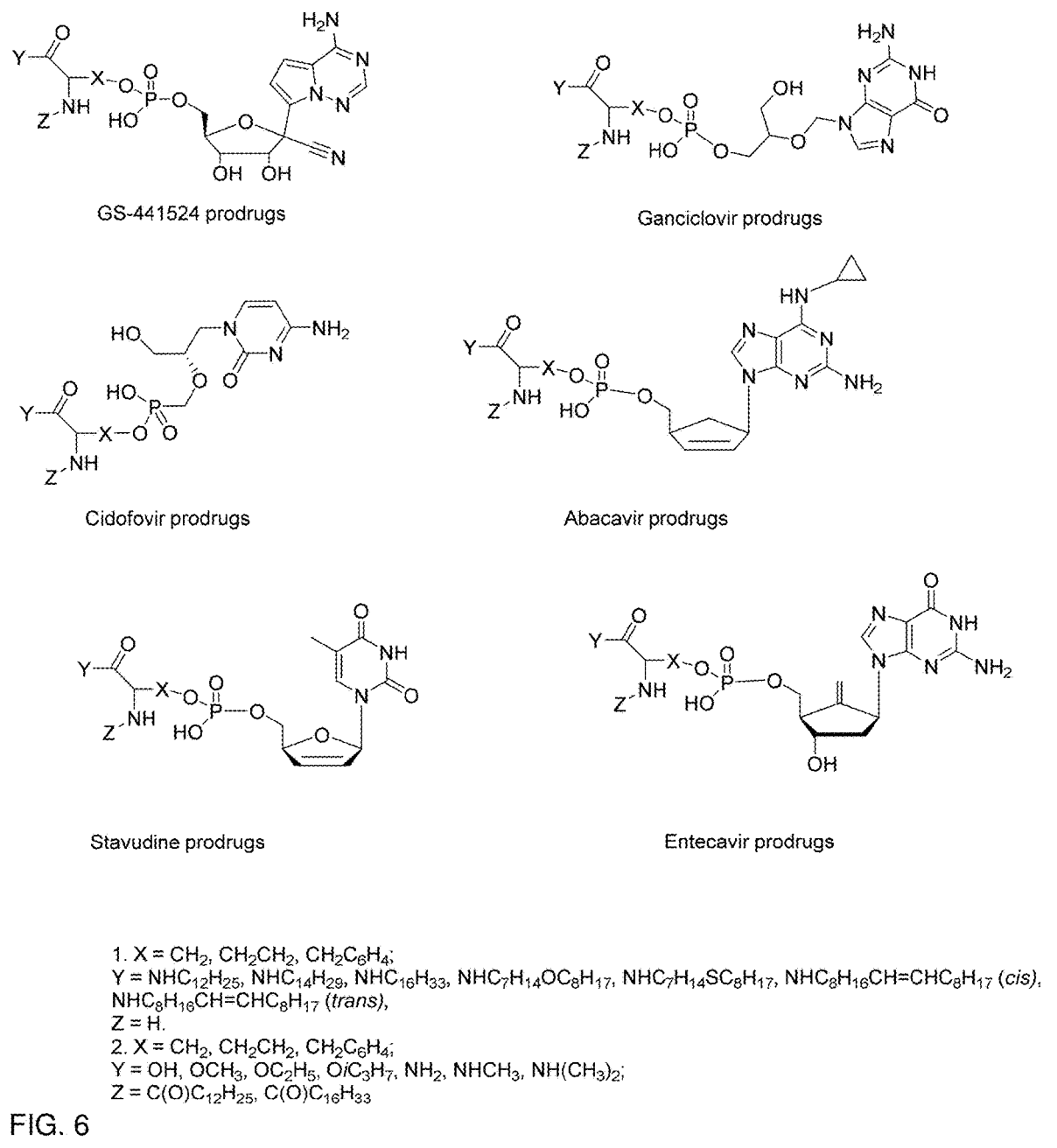

GS-441524 prodrugs

Ganciclovir prodrugs

Cidofovir prodrugs

Abacavir prodrugs

Stavudine prodrugs

Entecavir prodrugs

1. X = $CH_2$, $CH_2CH_2$, $CH_2C_6H_4$;
   Y = $NHC_{12}H_{25}$, $NHC_{14}H_{29}$, $NHC_{16}H_{33}$, $NHC_7H_{14}OC_8H_{17}$, $NHC_7H_{14}SC_8H_{17}$, $NHC_8H_{16}CH=CHC_8H_{17}$ (*cis*),
   $NHC_8H_{16}CH=CHC_8H_{17}$ (*trans*),
   Z = H.

2. X = $CH_2$, $CH_2CH_2$, $CH_2C_6H_4$;
   Y = OH, $OCH_3$, $OC_2H_5$, $OiC_3H_7$, $NH_2$, $NHCH_3$, $NH(CH_3)_2$;
   Z = $C(O)C_{12}H_{25}$, $C(O)C_{16}H_{33}$

FIG. 6

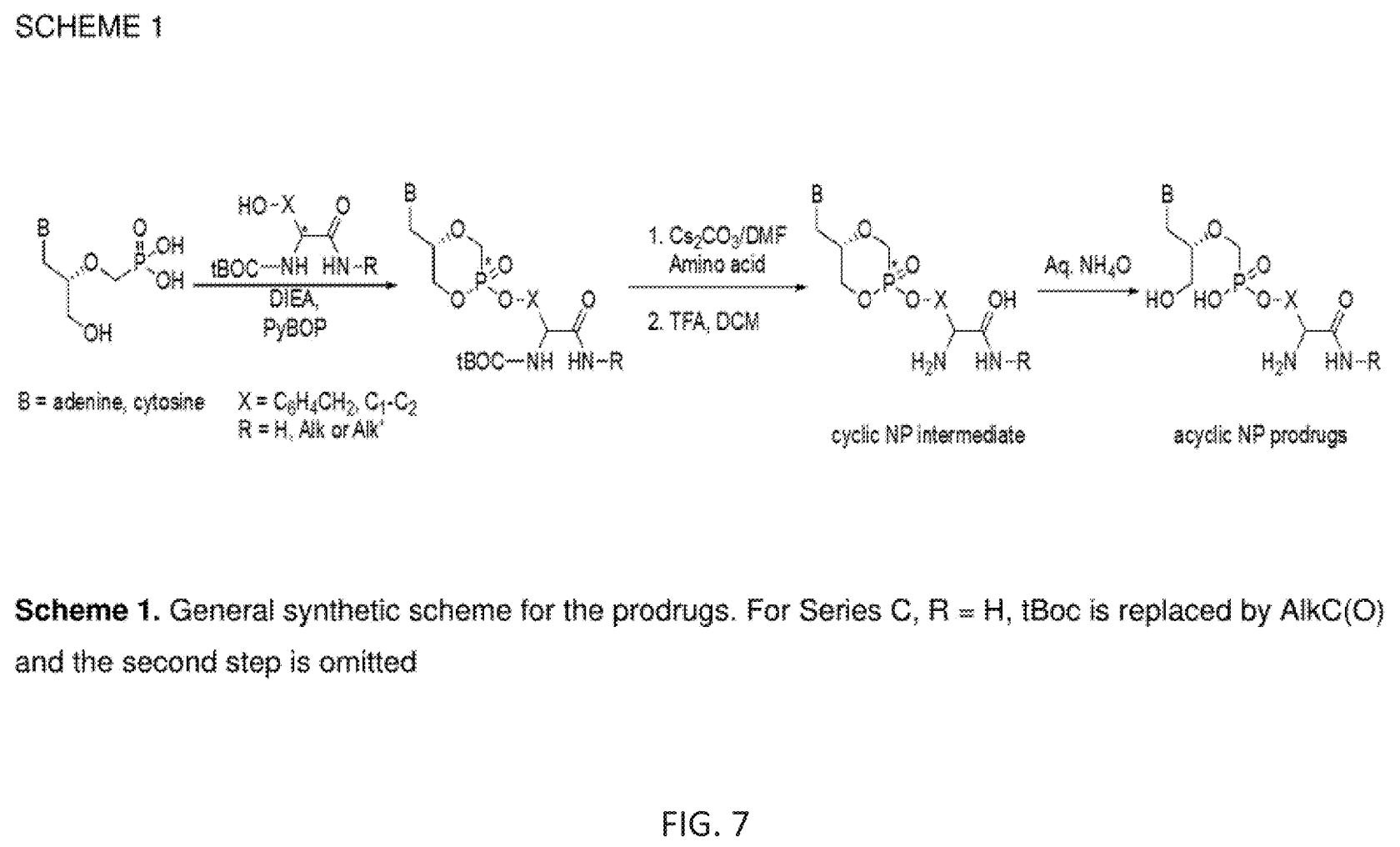

SCHEME 1

Scheme 1. General synthetic scheme for the prodrugs. For Series C, R = H, tBoc is replaced by AlkC(O) and the second step is omitted

FIG. 7

SCHEME 2

B = adenine, cytosine     X = C₆H₄CH₂, C₁-C₂
                          R = H, Alk or Alk'

Scheme 2. Alternative synthesis of prodrugs

FIG. 8

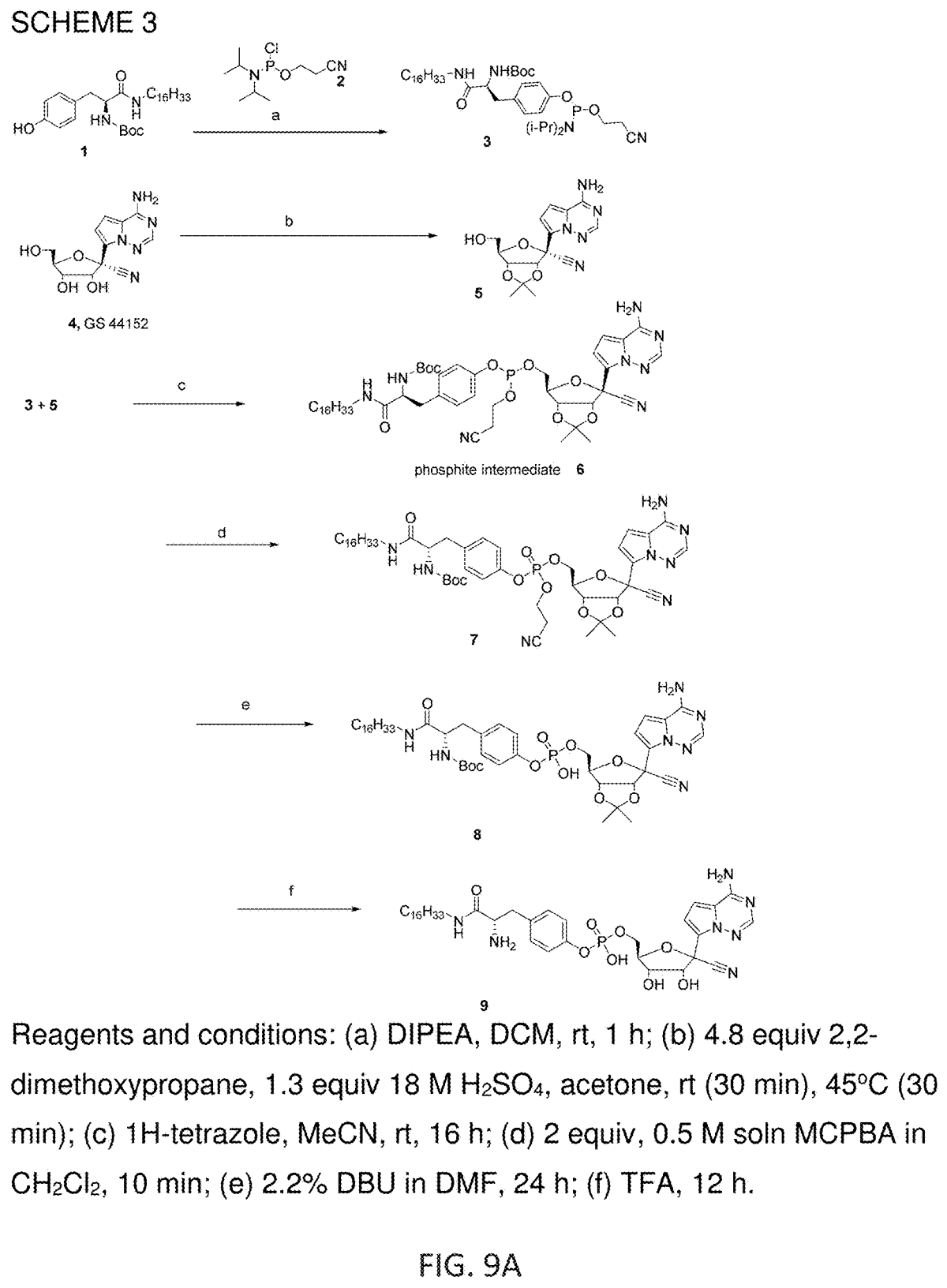

SCHEME 3

Reagents and conditions: (a) DIPEA, DCM, rt, 1 h; (b) 4.8 equiv 2,2-dimethoxypropane, 1.3 equiv 18 M $H_2SO_4$, acetone, rt (30 min), 45°C (30 min); (c) 1H-tetrazole, MeCN, rt, 16 h; (d) 2 equiv, 0.5 M soln MCPBA in $CH_2Cl_2$, 10 min; (e) 2.2% DBU in DMF, 24 h; (f) TFA, 12 h.

FIG. 9A

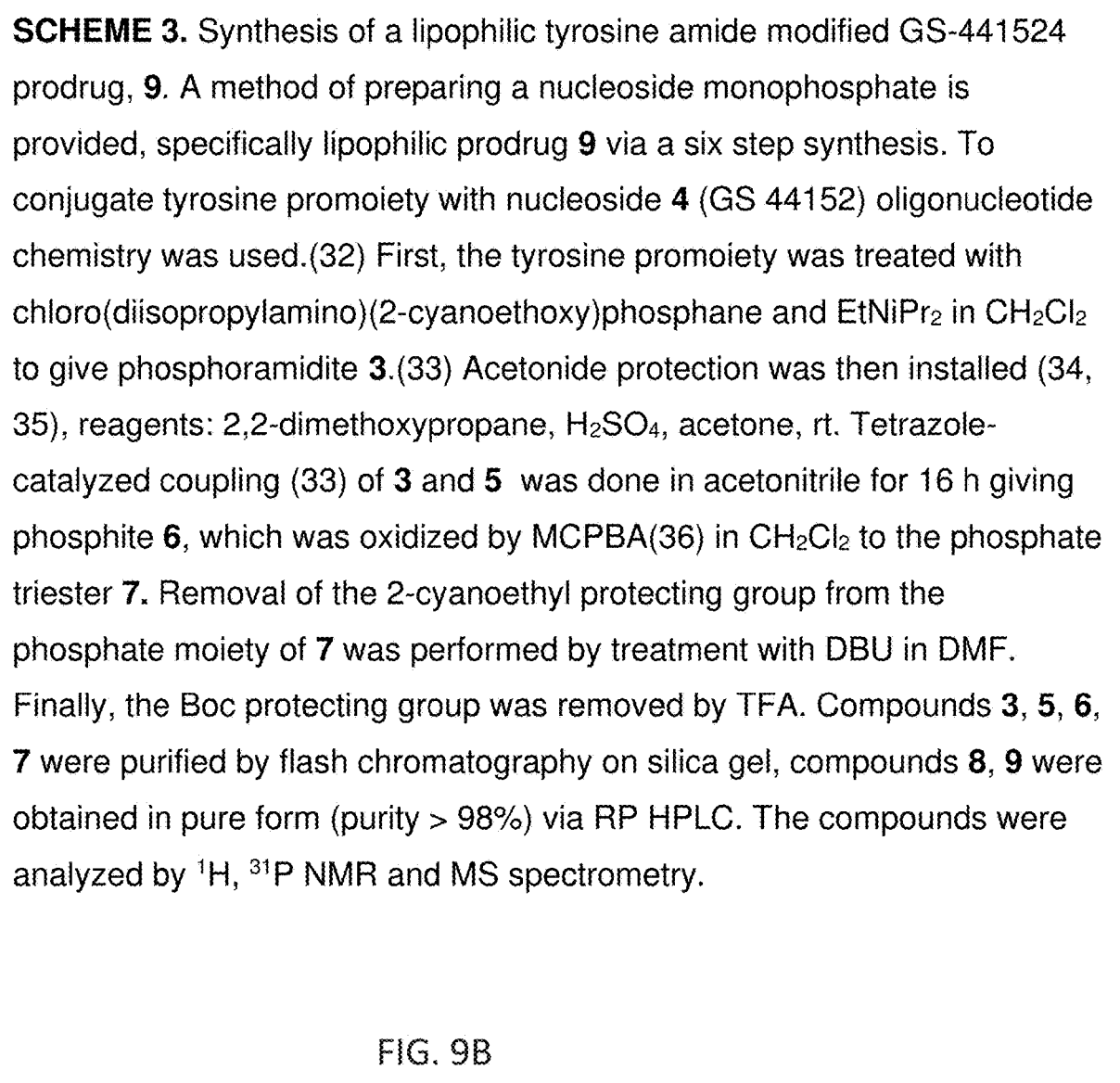

SCHEME 3. Synthesis of a lipophilic tyrosine amide modified GS-441524 prodrug, 9. A method of preparing a nucleoside monophosphate is provided, specifically lipophilic prodrug 9 via a six step synthesis. To conjugate tyrosine promoiety with nucleoside 4 (GS 44152) oligonucleotide chemistry was used.(32) First, the tyrosine promoiety was treated with chloro(diisopropylamino)(2-cyanoethoxy)phosphane and EtNiPr$_2$ in CH$_2$Cl$_2$ to give phosphoramidite 3.(33) Acetonide protection was then installed (34, 35), reagents: 2,2-dimethoxypropane, H$_2$SO$_4$, acetone, rt. Tetrazole-catalyzed coupling (33) of 3 and 5 was done in acetonitrile for 16 h giving phosphite 6, which was oxidized by MCPBA(36) in CH$_2$Cl$_2$ to the phosphate triester 7. Removal of the 2-cyanoethyl protecting group from the phosphate moiety of 7 was performed by treatment with DBU in DMF. Finally, the Boc protecting group was removed by TFA. Compounds 3, 5, 6, 7 were purified by flash chromatography on silica gel, compounds 8, 9 were obtained in pure form (purity > 98%) via RP HPLC. The compounds were analyzed by $^1$H, $^{31}$P NMR and MS spectrometry.

FIG. 9B

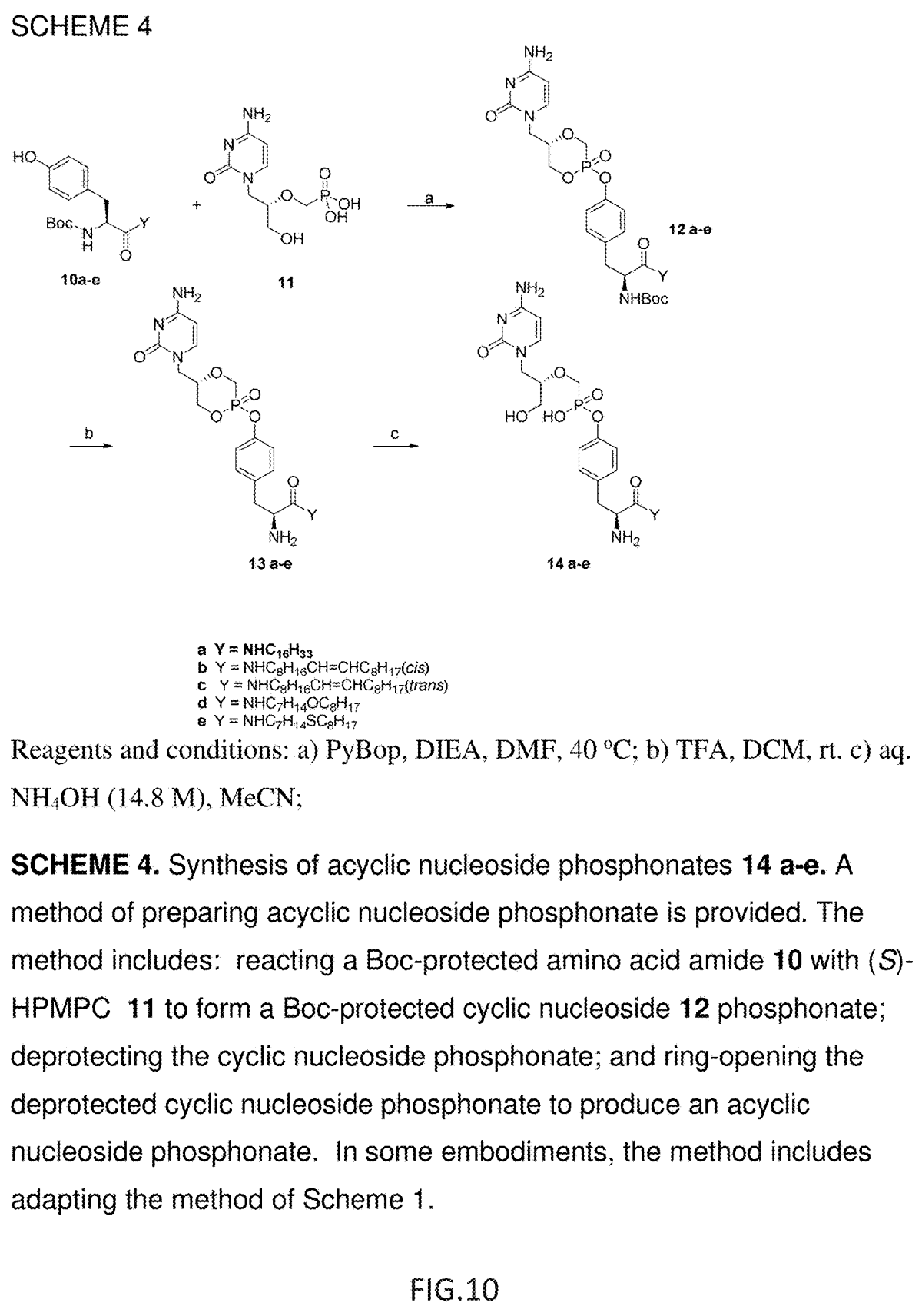

SCHEME 4 a   Y = NHC$_{16}$H$_{33}$
b   Y = NHC$_8$H$_{16}$CH=CHC$_8$H$_{17}$(cis)
c   Y = NHC$_8$H$_{16}$CH=CHC$_8$H$_{17}$(trans)
d   Y = NHC$_7$H$_{14}$OC$_8$H$_{17}$
e   Y = NHC$_7$H$_{14}$SC$_8$H$_{17}$ Reagents and conditions: a) PyBop, DIEA, DMF, 40 °C; b) TFA, DCM, rt. c) aq.
NH$_4$OH (14.8 M), MeCN;

SCHEME 4. Synthesis of acyclic nucleoside phosphonates 14 a-e. A
method of preparing acyclic nucleoside phosphonate is provided. The
method includes: reacting a Boc-protected amino acid amide 10 with (S)-
HPMPC 11 to form a Boc-protected cyclic nucleoside 12 phosphonate;
deprotecting the cyclic nucleoside phosphonate; and ring-opening the
deprotected cyclic nucleoside phosphonate to produce an acyclic
nucleoside phosphonate. In some embodiments, the method includes
adapting the method of Scheme 1.

FIG.10

PROMOIETY STRATEGY TO ENHANCE DRUG ACTIVITY

CROSS-REFERENCE TO RELATED APPLICATIONS

This application is the U.S. national phase of PCT Appln. No. PCT/US2021/046486 filed Aug. 18, 2021, which claims the benefit of U.S. Provisional Patent Application Ser. No. 63/067,204 filed, Aug. 18, 2020, the disclosures of which are hereby incorporated in their entirety by reference herein.

STATEMENT REGARDING FEDERALLY SPONSORED RESEARCH OR DEVELOPMENT

This invention was made with Government support under Grant No. from NIH DMID Services HHSN272201100022I, HHSN272201000021I, HHSN27200007, HHSN272201100016I, R21A1130927, R01AI135122. The Government has certain rights in this invention.

BACKGROUND

Field of the Invention

The invention relates to inhibition of nucleotide-binding enzymes such as nucleic acid polymerases and kinases to prevent or treat diseases.

Related Art

Nucleotide drugs are well-established in the prevention and treatment of diseases such as virus infections and cancer. A drawback of this approach is the poor bioavailability, low cell penetration, and toxicity of many nucleotide analogs, owing to their polarity and the charge of their ionized phosphate or phosphonate group(s). This can be exemplified by nucleoside phosphonate drugs used to treat virus infection.

Viral infection remains an evolving constellation of critical unmet health challenges. An example is human adenovirus (Ad) which has a linear duplex DNA genome that encodes about 35 genes and is enclosed in a protein capsid without a lipid membrane (1).

Adenovirus (Ad) is ubiquitous, infect most children, and generally cause asymptomatic or symptomatic infection of the respiratory, gastrointestinal, ocular, and other tissues that are usually self-limiting in healthy individuals with the exception of epidemic keratoconjunctivitis (1). However, Ad can cause serious infection in severely immunosuppressed individuals, especially in pediatric patients undergoing allogeneic hematopoietic stem cell transplantation (allo-HSCT), where the incidence of infection ranges from 5%-6% to 42%-47% depending on the study (2, 3). Mortality rates are up to 26% with symptomatic infection and up to 80% for disseminated disease (2, 3). In solid organ transplants, incidence ranges from 4% to 10% in pediatric liver transplants and up to 57% in small bowel recipients. Mortality can be as high as 18% in kidney transplants and 53% in liver transplants. With disseminated Ad disease, there is multiorgan involvement with Ad detected in peripheral blood, urine, bronchoalveolar fluid, and cerebrospinal fluid; death is associated with multi-organ failure and persisting or increasing levels of Ad in peripheral blood. Risk factors for Ad disease and death include young age, receipt of a mismatched and/or T cell-depleted graft, early and persistent isolation of Ad from multiple sites, high level of Ad in the blood, and increasing levels of Ad in stool beyond 106 genome copies per gram (2).

Despite the seriousness of Ad disease, there are no drugs currently approved to treat Ad infections. Intravenous gamma globulins have been employed, and intravenous cidofovir (CDV, HPMPC, (S)-1-(3-hydroxy-2-phosphonomethoxypropyl)cytosine) is used in many transplant clinics (4, 5), but controlled studies on the efficacy of these treatments have not been conducted. The DNA viruses are comprised of at least six distinct families of highly diverse viruses. The DNA polymerases that direct the replication of their genomes are well conserved and it is this characteristic that transcends the biologic differences among these viruses (6). This enzyme renders them susceptible to nucleoside phosphonate (NP) analogues that represent the predominant class of inhibitors for the treatment of DNA virus infections. CDV, a nucleoside phosphonate analogue of cytosine monophosphate (FIG. 1) is converted in cells to the CDV diphosphate analogue of dCTP, which is a preferred substrate for the Ad DNA polymerases, leading to chain termination and blocking viral replication.

Although CDV could in principle protect the target immunocompromised population from clinical manifestations associated with the DNA viruses, its clinical utility is limited by its modest efficacy, very low oral bioavailability (<5%) mandating i.v. or i.p. administration, and its dose limiting toxicity (7). CDV exhibits poor cellular uptake and is a substrate for organic anion transporter 1, leading to accumulation of CDV in renal tubules which causes nephrotoxicity (8).

A simple $C_{16}$ ether-linked propyl ester prodrug of CDV, brincidofovir (FIG. 1) (HDP-CDV, CMX001, BCV), has displayed improved efficacy against all the DNA viruses tested (9). BCV does not accumulate in renal tubules and shows little or no nephrotoxicity (10) but GI irritation has been a problematic serious side effect, suggesting premature activation of a portion of the oral dose in the GI tract (11, 12). BCV inhibits the replication of multiple Ad types in cell culture, with $EC_{50}$ values near 0.02 µM (13). BCV (and CDV) was also effective against Ad5 replication and pathogenesis in an immunosuppressed Syrian hamster model (14, 15). While BCV successfully suppressed infections during the first 10 weeks of administration, in a recent phase II clinical trial, infections arose after therapy was discontinued. BCV has also been recently evaluated in randomized placebo-controlled phase II clinical trial as a preemptive treatment for pediatric and adult allogenetic hematopoietic stem cell transplant (allo-HSCT) patients and patients with asymptomatic Ad viremia (16, 17). BCV treatment reduced Ad viremia in some of these patients however, the result was not statistically significant (17) and symptomatic GI irritation was observed. Drug induced diarrhea was also observed as a serious side effect of BCV in a phase 3 trial with CMV-infected patients (18, 19). As a result, the trials were discontinued (11).

Another example is SARS-CoV-2 which is responsible for a respiratory infection that can progress to severe pneumonia. COVID-19 has an estimated mortality rate of approximately 2-3.5%, which increases with age and the presence of comorbidities (e.g., hypertension, cardiac insufficiency, diabetes, and asthma). (20) Currently, laboratories and medical teams worldwide have focused on the repurposing of Food and Drug Administration (FDA)-approved drugs to treat the most severe cases of COVID-19, since there are no specific chemotherapeutic agents to treat this infection. Indeed, drug repositioning might be a short-term alternative to fight this disease. Since the efficacy, safety, and toxicity of these drugs are already well known, the initial phases of clinical trials could be skipped, which would reduce the cost and duration of the process. In general, drug repurposing is a cheaper, faster, and accessible way to make drugs available to the clinic. (21)

Several therapeutic agents have been evaluated for the treatment of SARS-Coronavirus-2 (SARS-CoV-2) disease (COVID-19), but none have yet been shown to be efficacious. The FDA recently issued an emergency use authorization (EUA) for remdesivir for COVID-19 even as it awaits more concrete evidence of benefit. (22) A double-blind, randomized, placebo-controlled trial of intravenous remdesivir (200 mg loading dose on day 1, followed by 100 mg daily for up to 9 additional days or placebo for up to 10 days) in adults hospitalized with Covid-19 with evidence of lower respiratory was conducted. (23) Preliminary clinical trial results suggest that there may be a favorable benefit-risk profile for remdesivir compared with placebo in severe COVID-19 infection and further data on benefits would strengthen this evaluation. (24) However, given high mortality despite the use of remdesivir, it is clear that treatment with this antiviral drug alone is not likely to be sufficient. (23) Besides, remdesivir can be administered only to hospitalized patients with severe illness defined as patients with low oxygen in blood or needing breathing assistance.

SUMMARY

The class of nucleotide analogue drugs includes both phosphonate and phosphates and are useful for the treatment of viral infections and cancer. Generally, these drugs suffer from lack oral bioavailability and other drawbacks arising from high polarity. Viral infections have been of increasing concern in a public health context due to the emergence of new pathogens and the potential for development of drug resistance among currently recognized viruses. Thus, the development of new, more effective antiviral compounds effective against existing and emerging pathogens is a high priority in medical research. Viral replication depends on the function of a viral DNA or RNA polymerase. The DNA viruses, which include herpes, cytomegalo-, varicella zoster, adeno-, pox, polyoma and papilloma viruses, have a requirement for DNA synthesis during their life cycle. This common element therefore becomes a target for broad spectrum antiviral compounds. Certain nucleoside phosphonates (NP), exemplified herein by cidofovir and its adenine analogue, HPMPA, have shown strong activity across a wide spectrum of DNA viruses. However, their development as antiviral drugs has been hampered by their inherent lack of bioavailability due to their highly polar nature. Our research at the University of Southern California (USC) has centered on overcoming the lack of oral bioavailability, low cellular permeability and tissue-specific toxicities of nucleoside phosphonate (NP) drugs by means of a novel prodrug strategy. These efforts have yielded a series of prodrugs of CDV and HPMPA with greatly enhanced in vitro antiviral potency against several DNA viruses, good oral absorption and significantly reduced risk of toxicity. Herein we disclose novel structural modifications of these prodrugs allowing their efficacy and pharmacological properties to be tuned advantageously. The invention of these useful promoiety modifications provides a wide range of compounds containing a modified phosphate, phosphonate or phosphinate group, including cyclic and acyclic NPs, with enhanced potency, oral availability, metabolism, cellular permeability and solubility) for inhibiting pathogenic viruses. Further-more, it can be applied to enhance the bioavailability and potency of nucleotide analogues designed to block repair polymerases in cancer cells to overcome their resistance to DNA-damaging chemotherapeutic drugs.

The RNA-dependent RNA polymerase (RdRp) of coronaviruses is a well-established drug target; the active site of the RdRp is highly conserved among positive-sense RNA viruses. These RdRps have low fidelity allowing them to recognize a variety of modified nucleotide analogues as substrates. Such nucleoside triphosphate analogues may inhibit further RNA polymerase catalyzed RNA replication making them important candidate anti-viral agents. Recent studies examined a library of nucleoside triphosphate (phosphonate) analogues for incorporation by the RdRps of SARS-CoV-2. (25) Of the 11 tested, 6 exhibited complete termination of the polymerase reaction, 2 showed incomplete or delayed termination. Five among them are triphosphate analogues of nucleoside drugs that are FDA approved medications for treatment of viral infections with established toxicity profiles. Thus, these five drugs and the parent nucleoside phosphate of remdesivir offer a molecular basis for the synthesis of prodrugs and their evaluation in SARS-CoV-2 virus inhibition. It will be appreciated by those skilled in the art that this list is not limiting, in that the prodrug approach disclosed in this invention can be readily used with any nucleoside phosphonate or nucleoside phosphate drug or drug precursor molecule.

During DNA/RNA replication, nucleosides are phosphorylated by various host cell kinases into their active triphosphate form, then are taken up by polymerases and incorporated into the growing chain. The same process is required for modified nucleosides, however, one of the major limitations to utilizing nucleosides as drugs is the specificity of the kinases involved in the various phosphorylation steps. These steps then become rate limiting for the overall conversion to the active triphosphate form. Since nucleoside analogues are not always recognized efficiently and thus may initially appear inactive, it became important to design analogues that could overcome this issue. In that regard, utilization of monophosphate analogues would be the best choice, however, the phosphate group renders the nucleotides extremely polar, therefore making it difficult for the compounds to cross the cellular membrane. This condition limits the therapeutic scope of these drugs. Moreover, after intravenous injection drugs of this class tend to accumulate in the kidney leading to renal toxicity. (8) Thus, there is a need for more effective, orally bioavailable forms of these drugs. Several prodrug approaches to improve oral absorption of antiviral nucleoside analogues by incorporating various phosphate or phosphonate anion masking groups have been developed. (26)

Recently, certain "tunable" prodrugs of CDV synthesized at the Univ. of Southern California (USC) have been demonstrated to be several orders of magnitude more potent against four Ad serotypes in vitro and orally effective against Ad6 in a Syrian hamster model. (27)

N-alkylated tyrosinamide ester modifications of CDV and HPMPA were found to exhibit up to three logs higher potency against Ad in infected HFF cells than the parent drug (28). Two of these compounds (FIG. 2) were highly effective orally in an Ad6 infection animal model (28). In addition, one of these was shown to be effective in vivo against a different DNA virus, VZV (29).

In the present application, compounds that comprise prodrugs with differing side chains derived from a natural amino acid (tyrosine, serine, homoserine, threonine) substance are provided in the form of an amide in which the amide substituent side chain is an alkyl, alkyl ether, thio-ether, or alkene. Embodiments of the compounds have a range of effective lipophilicity values allowing variation in aqueous solubility, oral bioavailability, cell permeability and in vivo activation properties. The embodiments have pro-moieties derived from a single amino acid, which are expected to have low toxicity. The features described above also make possible a novel "precision medicine" approach to treatment of viral infections, whereby the prodrug variations can be exploited to match optimal activation of the prodrug to a given patient or strain of virus.

Achieving the right balance in a given drug of potency, lipophilicity and hydrophilicity, permeability, chemical stability, rate, loci and extent of activation, safety and key physical properties, such as solubility, is a challenge. The strategy disclosed here involves a non-toxic amino acid prodrug moiety offering exceptional versatility for "tuning" potency and pharmacological properties by appropriate modification at one or more of multiple functionalizable sites (FIG. 3).

As summarized in FIG. 3, embodiments of the invention include incorporation of an O-Ser, O-homo-Ser, O-Thr or O-Tyr amino acid phosphonate ester linkage to the parent drug, with further modification of said linking group with a lipophilic group.

In another aspect, a nucleoside phosphonate (1) or nucleoside phosphate (2) is provided, having the formula $$\tag{1}$$

or $$\tag{2}$$

where: B is a natural or unnatural purine or pyrimidine base; X is $CH_2Ph$, $CH_2$, $CH_2CH_2$, or $CHCH_3$; Y is O, NH, $CH_2$, CHF, $CHC_1$, CHBr, $CF_2$, $CCl_2$, $CBr_2$, $CCH_3$, $C(CH_3)_2$, $CHN_3$, $CCH_3N_3$; Z is a cyclic or acyclic sugar, such as ribose or deoxyribose, or a related structure; m=0-1; $m_1$=0-3, $m_2$=0-3; R is H or $C(O)R_2$, wherein $R_2$ is lipid-like; and $R_1$ is H or lipid-like. In addition, the $NHR_1$ group in (1) may be replaced by $OR_3$, wherein $R_3$=a $C_1$-$C_4$ alkyl, when R=C(O)R_2$, with $R_2$ defined as above.

In some embodiments: a) $R_1/R_2$ is alkyl, which can be a long-chain alkyl, which can be $C_{8-18}$ alkyl; b) $R_1/R_2$ is alkyl, alkene, ether or thioether, which can be $C_{12-18}$ alkyl, $(CH_2)_mCH=CHC_{n1}$, $(CH_2)_n$—O—$(CH_2)_{n1}$, or $(CH_2)_m$—S—$(CH_2)_{n1}$ wherein n and/or n1=4-9; or any combination of a)-b).

In some embodiments, nucleoside phosphonates (3) and (4) are provided, having the formula

6

$$\tag{3}$$

or $$\tag{4}$$

wherein B, X, R and $R_1$ are as defined in the two preceding paragraphs.

In some embodiments, B is an adenine or cytosine. In other embodiments B is a natural or unnatural purine or pyrimidine. B may form a natural or unnatural nucleoside.

In some embodiments of the foregoing, B and Z correspond to a nucleoside compound effective against virus infections or cancer. Examples of viruses are SARS-CoV-2, adenovirus, cytomegalovirus and varicella zoster virus.

In some embodiments in formulas 3 and 4, R=H and $R_1$ is defined as in paragraphs 0020 and 0021.

In some embodiments in formulas 3 and 4, $R_1$=H or $OR_3$ and R=C(O)R_2$ where $R_3$ and $R_2$ are defined as in paragraphs 0020 and 0021.

In another aspect, any nucleoside phosphonate or phosphate described in FIGS. 3, 4, 6 and in Schemes 1 and 2, is an embodiment of the invention.

In a further aspect, a method of preparing a nucleoside phosphonate is provided. The method includes selective dealkylation of a mixed phosphonate monoalkyl diester by bromotrimethylsilane (BTMS), as illustrated by the example in the following reaction scheme:

-continued where: B is a natural or unnatural purine or pyrimidine base; R is H or C(O)R$_2$, wherein R$_2$ is lipid-like; and R$_1$ is NHR$_{1a}$, where R$_{1a}$ is H or lipid-like.

In some embodiments of the method: a) B is cytosine or adenine; b) R$_2$ is alkyl, which can be C$_{8-18}$ alkyl; c) R$_{1a}$ is alkyl, alkene, ether or thioether, which can be C$_{12-18}$ alkyl, (CH$_2$)$_n$CH=CHC$_{n1}$, (CH$_2$)$_n$—O—(CH$_2$)$_{n1}$ or (CH$_2$)$_n$—S—(CH$_2$)$_{n1}$ wherein n and/or n1=4-9; d) the CH$_2$Ph group can be replaced by CH$_2$, CH$_2$CH$_2$, or CHCH$_3$; or any combination of a) d)

In a further aspect, a method of preparing a nucleoside phosphate is provided. The method includes CDI conjugation of a phosphorylated amino acid with pyrophosphate or pyrophosphate analogues, as outlined in the following reaction scheme:

where B is a purine or pyrimidine base; R is H or C(O) NHR$_2$, wherein R$_2$ is lipid-like; and R$_1$ is NHR$_{1a}$, where R$_{1a}$ is H or lipid-like.

In some embodiments of the method: a) B is cytosine, guanine, adenine or thymine, or a related structure; b) R$_2$ is alkyl, which can be C$_{8-18}$ alkyl; c) R$_{1a}$ is alkyl, alkene, ether or thioether, which can be C$_{12-18}$ alkyl, (CH$_2$)$_n$CH—CHC$_{n1}$, (CH$_2$)$_n$—O—(CH$_2$)$_{n1}$ or (CH$_2$)$_n$—S—(CH$_2$)$_{n1}$ wherein n and/or n1=4-9; d) the CH$_2$Ph group can be replaced by CH$_2$, CH$_2$CH$_2$, or CHCH$_3$; e) Y is O, NH, CH$_2$, CHF, CHCl, CHBr, CF$_2$, CCl$_2$, CBr$_2$, CCH$_3$, C(CH$_3$)$_2$, CHN$_3$, CCH$_3$N$_3$; or CCH$_3$N$_3$; f) Z is a ribose or deoxy ribose sugar, or a related structure; m=0-1; m$_1$=0-3; m$_2$=0-3; or any combination of a)-f).

In another aspect, a pharmaceutical composition that includes a nucleoside phosphonate is provided. The pharmaceutical composition includes one or more of the nucleoside phosphonates described herein, and a pharmaceutically acceptable carrier.

In a further aspect, a method of treating an adenovirus, coronavirus, varicella zoster or other virus infection in a subject in need thereof is provided. The method includes administering to the subject an effective amount of one or more of the nucleoside phosphonates described herein, or an effective amount of a pharmaceutical composition containing one or more of the nucleoside phosphonates described herein. The subject can be a human or other animal, such as another mammal.

In some embodiments, a method of treating cancer is provided. The method includes administering to the subject an effective amount of at least one nucleoside phosphonate or nucleoside phosphate described herein.

The following Examples describe the synthesis of embodiments of the prodrug compounds. The present invention may be better understood by referring to the accompanying examples, which are intended for illustration purposes only and should not in any sense be construed as limiting the scope of the invention.

BRIEF DESCRIPTION OF THE DRAWINGS

For a more complete understanding of the present invention, reference is now made to the following descriptions taken in conjunction with the accompanying drawings, in which:

Figures 1, 2:
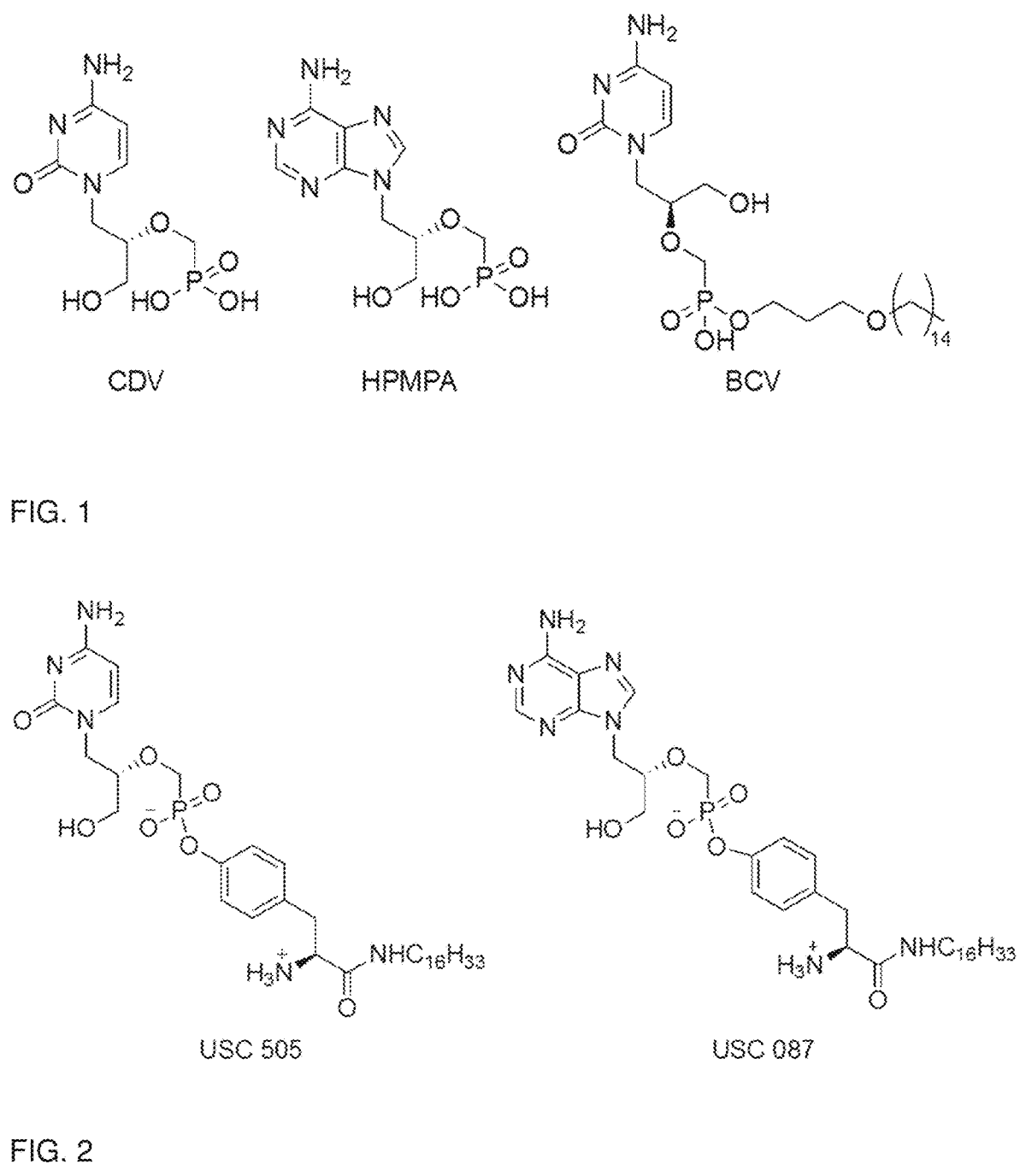

FIG. 1 is a panel showing the structures of CDV, HPMPA and BCV.

FIG. 2 is a panel showing the structures of USC-505 and USC-087.

FIG. 3 is a general schematic representation of the prodrug linker platform to increase oral bioavailability and potency of NP drugs. The phosphonic acid group is esterified by the OH side-chain X of an amino acid that has a free (R=H) or modified (R=C(O)NHR$_2$, R$_2$=lipophilic modifier) $\alpha$-amino group or a modified $\alpha$-carboxyl group where R$_1$=H, lipid-like.

FIG. 4 is a table showing embodiments of this invention, in terms of the lipophilic modifier structure (Series A, B), lipid modifier location (Series C), and the linking hydroxy side chain of the esterifying amino acid promoiety (Series D). Range of n and/or n1=4-9.

Figure 5:
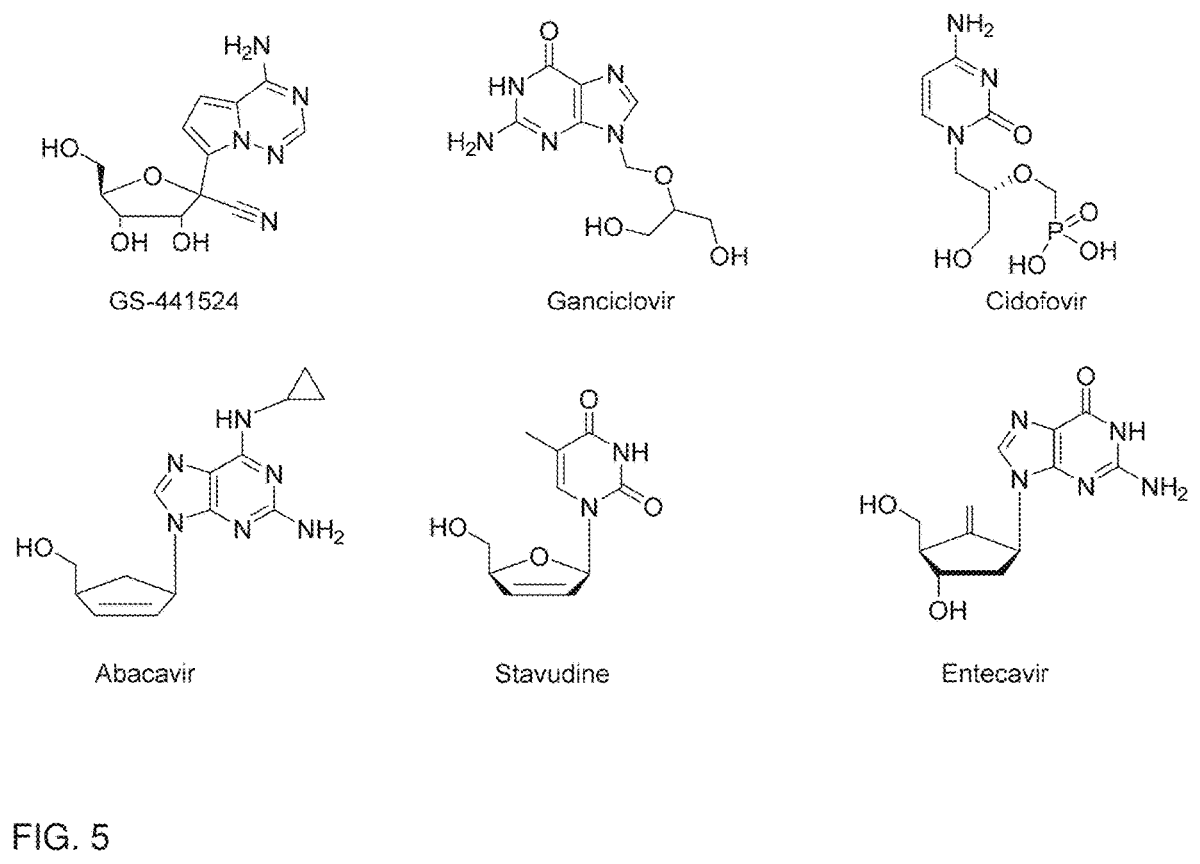

FIG. 5 is a panel of known drugs exhibiting termination of the RdRps of SARS-CoV-2 (25).

FIG. 6 is a panel of general structures of examples of the new lipophilic prodrugs.

FIG. 7 provides Scheme 1 which is a general synthetic scheme for the prodrugs. For Series C, R=H, tBOC is replaced by AlkC(O) and the second step is omitted.

Figure 8:
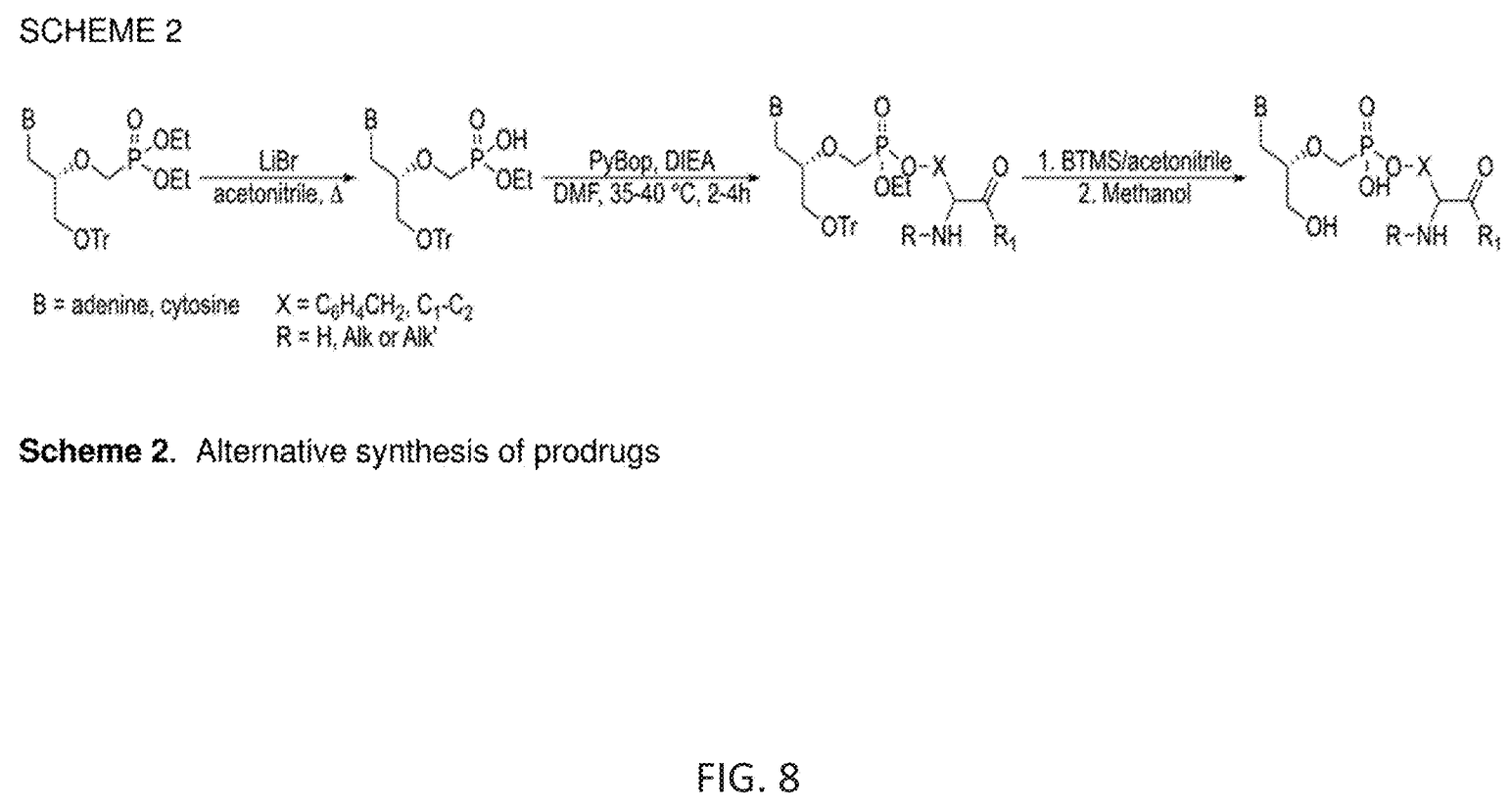

FIG. 8 provides Scheme 2 which is a alternative synthesis of the prodrugs.

FIGS. 9A and 9B provide Scheme 3 which exemplifies a synthesis of a lipophilic tyrosineamide-modified GS-441524 prodrug.

FIG. 8 provides Scheme 4 which exemplifies a method of preparing certain nucleoside monophosphates.

DETAILED DESCRIPTION

In methods of treating virus infection or inhibiting virus replication, an effective amount, which can be a therapeutically effective amount, of an acyclic nucleoside phosphonate, or a salt or pharmaceutically acceptable salt thereof, may be administered. A therapeutically effective amount of a compound is an amount that results in an improvement or a desired change in condition for which a compound is administered, when the compound is administered once or over a period of time. For example, with respect to virus infections, the improvement can be a lowering of virus titer, or a reduction in the symptoms or discomfort associated with a viral infection. As is known, the amount will vary depending on such particulars as the type of virus infection, the condition being treated, the specific acyclic nucleoside phosphonate compound utilized, the severity of the condition, and the characteristics of the subject. The subject can be a person or another animal, such as another mammal.

An antiviral compound such as a nucleoside phosphonate can be prepared as a salt, which may be a pharmaceutically acceptable salt. Pharmaceutically acceptable salts are well known in the art and include salts prepared from pharmaceutically acceptable non-toxic acids, including inorganic acids and organic acids. Suitable non-toxic acids include inorganic and organic acids such as acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic acids, and the like. Salts formed with, for example, a POH group, can be derived from inorganic bases including, but not limited to, sodium, potassium, ammonium, calcium or ferric hydroxides, and organic bases including, but not limited to, isopropylamine, trimethylamine, histidine, and procaine.

Pharmaceutical compositions containing nucleoside phosphonates will typically contain a pharmaceutically acceptable carrier. Although oral administration is a desired route of administration, other means of administration such as nasal, topical (for example, administration to the skin or eye) or rectal administration, or by injection or inhalation, are also contemplated. Depending on the intended mode of administration, the pharmaceutical compositions may be in the form of solid, semi-solid or liquid dosage forms, such as, for example, tablets, suppositories, pills, capsules, powders, liquids, suspensions, drops, ointments, creams or lotions, preferably in unit dosage form suitable for single administration of a precise dosage. The compositions may include an effective amount of a selected compound in combination with a pharmaceutically acceptable carrier and, in addition, may include other pharmaceutical agents such as other anti-viral agents, adjuvants, diluents, buffers, and the like. The compound may thus be administered in dosage formulations containing conventional non-toxic pharmaceutically acceptable carriers, adjuvants and vehicles. The amount of active compound administered will be dependent on the subject being treated, the subject's weight, the manner of administration and the judgment of the prescribing physician.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions may, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan mono-laurate, triethanolamine acetate, triethanolamine oleate, etc. Actual methods of preparing such dosage forms are known, or will be apparent, to those skilled in this art. For oral administration, the composition will generally take the form of a tablet or capsule, or may be an aqueous or nonaqueous solution, suspension or syrup. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

In embodiments that include a method of inhibiting viral replication or a method of treating a virus infection, the virus may be an RNA virus, a DNA virus, or a retrovirus, for example. Particular examples of viruses include, but are not limited to, severe acute respiratory syndrome coronavirus 2 (SARS-CoV-2), varicella zoster virus (VZV), human pap-ililomavirus (HPV), cytomegalovirus (CMV).

The present invention may be better understood by refer-ring to the accompanying examples, which are intended for illustration purposes only and should not in any sense be construed as limiting the scope of the invention.

EXAMPLE 1

Synthesis of CDV and HPMPA Prodrugs
Example 1a. General Synthesis of Novel Prodrugs The structures of embodiments of this invention are shown in FIG. 4 (Series A-D). As in which structural features are changed to modify biological and pharmaco-logical properties of the prodrugs: i) lipophilic chain length and structure (Series A); by introducing unsaturation at the center of the N-alkyl group; ii) introduction of a polar atom (O or S) at the center of the lipid modifier to create a site for enzymatic cleavage to decrease lipidomimetic properties of the prodrug in the cell prior to P—O ester cleavage or a means to increase prodrug aqueous solubility without reduc-ing the chain length with only a modest (ΔpD~−1) impact on lipophilicity (Series B); iii) variation in the position of the N-alkyl chain by moving it to the amino side of the pro-moiety (Series C); this modification converts the prodrug from a zwitterion (more lipidomimetic) to a monoamine PO⁻ (more soluble in aqueous media); iv) the amino acid P—O ester linkage (O-Tyr, O-Ser, O-Homo-Ser or O-Thr) to vary metabolic activation and other PK properties to tune enzyme-dependent activation of the prodrug by cellular phospholipases/phosphatases (Series D). The person skilled in the art will appreciate that by some of the modifications taught in this invention or similar ones, it is possible to modulate the overall charge on the prodrug molecule and specifically, its promoiety to advantage. For example, intro-duction of a positive charge by retention of the free amino group and neutralization of the remaining negative charge of the esterified phosphonic acid group by conversion to a cyclic, amido or simple alkyl or aryl ester forms.
Experimental General syntheses of the lipidomimetic synthons: Com-mercially unavailable N-alkyl promoieties can be synthe-sized by literature methods (30-32).

Conjugation of the lipidomimetic synthons to (S)-HPMPC and (S)-HPMPA: Prodrugs that incorporate a derivatized single amino acid having a hydroxy side chain in the promoiety portion of the molecule can be prepared following the generalized synthetic pathway shown in Scheme 1 (33). The conjugation of the amino acid promoi-eties to CDV (or HPMPA) via an internal phosphoester bond in the penultimate synthetic step produces a new chiral center at phosphorus ($S_p$ or $R_p$), however these cyclic NP intermediates, generated as diastereomeric mixtures, are converted to the same final nucleoside phosphonate ana-logue in the last step. (The cyclic phosphonate intermediates are themselves active prodrugs (34) but have different metabolic $t_{1/2}$ and require an additional purification step for individual isolation. They are considered as further embodi-ments of this invention, providing a neutral phosphonate group in the final prodrug structure, which may be advan-tageous as explained in the preceding paragraph. The tBoc-protected amino acid synthons can be prepared by a previ-ously described method (33). Alkenyl lipophilic substituent (Series A) precursors are advantageously 1-aminoalkenes (cis or trans) which can be added to N-tBoc-protected amino acids by reaction with HOBt/EDC in DCM at 25° C. Alkoxyalkyl lipophilic substituents (Series B) can be pre-pared as follows: 1) (example, $C_8$—O—$C_8$): 8-bromo-1-octanal is converted to the phtalimide alcohol in DMF, then reacted with 1-bromooctane and NaH in DMF, and depro-tected with hydrazine in EtOH; 2) (example, $C_8$—S—$C_8$): 1,8-dibromooctane is similarly monoprotected, then reacted with 1-bromooctane and NaOH in thiourea.

Example 1b. Large-scale Syntheses of Analogues.

For large-scale synthesis, the known chemoselectivity of BTMS-silyldealkylation (35, 36) for alkyl (i.e., ethyl or methyl) vs. aryl (i.e., tyrosinyl) or sterically larger than methyl (i.e. serinyl, homoserinyl, threonilyl) phosphonate esters can be utilized. Elimination of the $NH_4OH$ hydrolysis step in Scheme 1, which typically limits the overall yield (~50%), makes this method attractive for further scaling development. An important feature of this new method is that it allows the intermediates to be purified by silica gel column chromatography, avoiding preparative HPLC which may be impractical and too time-consuming for large-scale synthesis. After BTMS deprotection, the final products can also be isolated by crystallization, which is highly scalable.

REFERENCES

The following publications are incorporated by reference herein in their entireties:

1. Wold W S M, Ison M G. Adenoviruses. In: Knipe D M, Howley P M, editors. Fields Virology. Philadelphia, PA: Lippincott Williams & Wilkins; 2013. p. 1732.
2. Lion T. Adenovirus infections in immunocompetent and immunocompromised patients. Clin Microbiol Rev. 2014. 27(3):441-462. Epub 2014 Jul. 2. doi: 10.1128/CMR.00116-13.
3. Sandkovsky U, Vargas L, Florescu D F. Adenovirus: current epidemiology and emerging approaches to pre-vention and treatment. Curr Infect Dis Rep. 2014. 16(8): 416. Epub 2014 Jun. 9. doi: 10.1007/s11908-014-0416-y.
4. Saquib R, Melton L B, Chandrakantan A, Rice K M, Spak C W, Saad R D, Fenves A Z, Barri Y M. Disseminated adenovirus infection in renal transplant recipients: the role of cidofovir and intravenous immunoglobulin. Transpl Infect Dis. 2010. 12(1):77-83. Epub 2009 Sep. 19. doi: 10.1111/j.1399-3062.2009.00452.x.
5. Neofytos D, Ojha A, Mookerjee B, Wagner J, Filicko J, Ferber A, Dessain S, Grosso D, Brunner J, Flomenberg N, Flomenberg P. Treatment of adenovirus disease in stem cell transplant recipients with cidofovir. Biol Blood Mar-row Transplant. 2007. 13(1):74-81. Epub 2007 Jan. 16. doi: 10.1016/j.bbmt.2006.08.040.
6. Wold W S, Toth K. New drug on the horizon for treating adenovirus. Expert Opin Pharmacother. 2015. 16(14): 2095-2099. Epub 2015 Sep. 4. doi: 10.1517/14656566.2015.1083975.
7. Cundy K C, Bidgood A M, Lynch G, Shaw J P, Griffin L, Lee W A. Pharmacokinetics, bioavailability, metabolism, and tissue distribution of cidofovir (HPMPC) and cyclic HPMPC in rats. Drug Metab Dispos. 1996. 24(7):745-752. Epub 1996 Jul. 1.

8. Izzedine H, Launay-Vacher V, Deray G. Antiviral drug-induced nephrotoxicity. Am J Kidney Dis. 2005. 45(5):804-817. Epub 2005 Apr. 30. doi: 10.1053/j.ajkd.2005.02.010.

9. Williams-Aziz S L, Hartline C B, Harden E A, Daily S L, Prichard M N, Kushner N L, Beadle J R, Wan W B, Hostetler K Y, Kern E R. Comparative activities of lipid esters of cidofovir and cyclic cidofovir against replication of herpesviruses in vitro. Antimicrob Agents Chemother. 2005. 49(9):3724-3733. Epub 2005 Aug. 30. doi: 10.1128/AAC.49.9.3724-3733.2005.

10. Hostetler K Y. Alkoxyalkyl prodrugs of acyclic nucleoside phosphonates enhance oral antiviral activity and reduce toxicity: current state of the art. Antiviral Res. 2009. 82(2):A84-98. Epub 2009 May 9. doi: 10.1016/j.antiviral.2009.01.005.

11. de la Camara R. CMV in Hematopoietic Stem Cell Transplantation. Mediterr J Hematol Infect Dis. 2016. 8(1):e2016031. Epub 2016 Jul. 15. doi: 10.4084/MJHID.2016.031.

12. Lanier R, Trost L, Tippin T, Lampert B, Robertson A, Foster S, Rose M, Painter W, O'Mahony R, Almond M, Painter G. Development of CMX001 for the Treatment of Poxvirus Infections. Viruses. 2010. 2(12):2740-2762. Epub 2011 Apr. 19. doi: 10.3390/v2122740.

13. Hartline C B, Gustin K M, Wan W B, Ciesla S L, Beadle J R, Hostetler K Y, Kern E R. Ether lipid-ester prodrugs of acyclic nucleoside phosphonates: activity against adenovirus replication in vitro. J Infect Dis. 2005. 191(3):396-399. Epub 2005 Jan. 6. doi: 10.1086/426831.

14. Tollefson A E, Spencer J F, Ying B, Buller R M, Wold W S, Toth K. Cidofovir and brincidofovir reduce the pathology caused by systemic infection with human type 5 adenovirus in immunosuppressed Syrian hamsters, while ribavirin is largely ineffective in this model. Antiviral Res. 2014. 112:38-46. Epub 2014 Dec. 3. doi: 10.1016/j.antiviral.2014.10.005.

15. Toth K, Spencer J F, Dhar D, Sagartz J E, Buller R M, Painter G R, Wold W S. Hexadecyloxypropyl-cidofovir, CMX001, prevents adenovirus-induced mortality in a permissive, immunosuppressed animal model. Proc Natl Acad Sci USA. 2008. 105(20):7293-7297. Epub 2008 May 21. doi: 10.1073/pnas.0800200105.

16. Paolino K, Sande J, Perez E, Loechelt B, Jantausch B, Painter W, Anderson M, Tippin T, Lanier E R, Fry T, DeBiasi R L. Eradication of disseminated adenovirus infection in a pediatric hematopoietic stem cell transplantation recipient using the novel antiviral agent CMX001. J Clin Virol. 2011. 50(2):167-170. Epub 2010 Nov. 26. doi: 10.1016/j.jcv.2010.10.016.

17. Grimley M S, Chemaly R F, Englund J A, Kurtzberg J, Chittick G, Brundage T M, Bae A, Morrison M E, Prasad V K. Brincidofovir for Asymptomatic Adenovirus Viremia in Pediatric and Adult Allogeneic Hematopoietic Cell Transplant Recipients: A Randomized Placebo-Controlled Phase II Trial. Biol Blood Marrow Transplant. 2017. 23(3):512-521. Epub 2017 Jan. 9. doi: 10.1016/j.bbmt.2016.12.621.

18. Marty F M, Winston D J, Chemaly R F, Boeckh M J, Mullane K M, Shore T B, Papanicolaou G A, Morrison M E, Brundage T M, Mommeja-Marin H. Brincidofovir for Prevention of Cytomegalovirus (CMV) after Allogeneic Hematopoietic Cell Transplantation (HCT) in CMV-Seropositive Patients: A Randomized, Double-Blind, Placebo-Controlled, Parallel-Group Phase 3 Trial. Biology of Blood and Marrow Transplantation. 2016. 22(3):S23-S23.

19. Marty F M, Winston D J, Rowley S D, Vance E, Papanicolaou G A, Mullane K M, Brundage T M, Robertson A T, Godkin S, Mommeja-Marin H, Boeckh M, Group CMXCS. CMX001 to prevent cytomegalovirus disease in hematopoietic-cell transplantation. N Engl J Med. 2013. 369(13):1227-1236. Epub 2013 Sep. 27. doi: 10.1056/NEJMoa1303688.

20. Lima W G, Brito J C M, Overhage J, Nizer W. The potential of drug repositioning as a short-term strategy for the control and treatment of COVID-19 (SARS-CoV-2): a systematic review. Arch Virol. 2020. 165(8):1729-1737. Epub 2020 Jun. 10. doi: 10.1007/s00705-020-04693-5.

21. Guy R K, DiPaola R S, Romanelli F, Dutch R E. Rapid repurposing of drugs for COVID-19. Science. 2020. 368(6493):829-830. Epub 2020 May 10. doi: 10.1126/science.abb9332.

22. Mullard A. Hints of hope with remdesivir. Nat Rev Drug Discov. 2020. 19(6):373. Epub 2020 May 13. doi: 10.1038/d41573-020-00088-y.

23. Beigel J H, Tomashek K M, Dodd L E, Mehta A K, Zingman B S, Kalil A C, Hohmann E, Chu H Y, Luetkemeyer A, Kline S, Lopez d C D, Finberg R W, Dierberg K, Tapson V, Hsieh L, Patterson T F, Paredes R, Sweeney D A, Short W R, Touloumi G, Lye D C, Ohmagari N, Oh M-D, Ruiz-Palacios G M, Benfield T, Fatkenheuer G, Kortepeter M G, Atmar R L, Creech C B, Lundgren J, Babiker A G, Pett S, Neaton J D, Burgess T H, Bonnett T, Green M, Makowski M, Osinusi A, Nayak S, Lane H C. Remdesivir for the Treatment of Covid-19—Preliminary Report. N Engl J Med. 2020.

24. Davies M, Osborne V, Lane S, Roy D, Dhanda S, Evans A, Shakir S. Remdesivir in Treatment of COVID-19: A Systematic Benefit-Risk Assessment. Drug Saf. 2020. 43(7):645-656. Epub 2020 May 30. doi: 10.1007/s40264-020-00952-1.

25. Jockusch S, Tao C, Li X, Anderson T K, Chien M, Kumar S, Russo J J, Kirchdoerfer R N, Ju J. A library of nucleotide analogues terminate RNA synthesis catalyzed by polymerases of coronaviruses that cause SARS and COVID-19. Antiviral Res. 2020. 180:104857. Epub 2020 Jun. 21. doi: 10.1016/j.antiviral.2020.104857.

26. Peterson L W, McKenna C E. Prodrug approaches to improving the oral absorption of antiviral nucleotide analogues. Expert Opin Drug Deliv. 2009. 6(4):405-420. Epub 2009 Apr. 23. doi: 10.1517/17425240902824808.

27. Toth K, Spencer J F, Ying B, Tollefson A E, Hartline C B, Richard E T, Fan J, Lyu J, Kashemirov B A, Harteg C, Reyna D, Lipka E, Prichard M N, McKenna C E, Wold W S M. USC-087 protects Syrian hamsters against lethal challenge with human species C adenoviruses. Antiviral Res. 2018. 153:1-9. Epub 2018 Mar. 7. doi: 10.1016/j.antiviral.2018.03.001.

28. Toth K, Spencer J, Tollefson A E, Ying B, Wold W, Reyna D, Ganesan S, Harteg C, Lipka E, Richard E, Lv J, Fan J, Kashemirov B, McKenna C, Prichard M. USC-087 and USC-505 Protect Immunosuppressed Syrian Hamsters Against Lethal Intravenous Challenge with Human Type 5 and 6 Adenoviruses. 29th International Conference on Antiviral Research (ICAR). 2016. La Jolla, CA.

29. Moffat J, Liu D, Coombs W, Reyna D, Ganesan S, Harteg C, Lipka E, Richard E, Lv J, Fan J, Kashemirov B, McKenna C, Prichard M. Tyrosine Ester Prodrug of Cidofovir is Effective Against VZV in Mice. 29th International Conference on Antiviral Research (ICAR). 2016. La Jolla, CA.

30. Grimm J B, Wilson K J, Witter D J. Suppression of racemization in the carbonylation of amino acid-derived aryl triflates. Tetrahedron Letters. 2007. 48(26):4509-4513. doi: 10.1016/j.tetlet.2007.04.145.

31. Kikuchi C, Nagaso H, Hiranuma T, Koyama M. Tetra-hydrobenzindoles: selective antagonists of the 5-HT7 receptor. J Med Chem. 1999. 42(4):533-535. Epub 1999 Mar. 3. doi: 10.1021/jm980519u.

32. Zakharova V M, Serpi M, Krylov I S, Peterson L W, Breitenbach J M, Borysko K Z, Drach J C, Collins M, Hilfinger J M, Kashemirov B A, McKenna C E. Tyrosine-based 1-(S)-[3-hydroxy-2-(phosphonomethoxy)propyl] cytosine and -adenine ((S)-HPMPC and (S)-HPMPA) prodrugs: synthesis, stability, antiviral activity, and in vivo transport studies. J Med Chem. 2011. 54(16):5680-5693. Epub 2011 Aug. 5. doi: 10.1021/jm2001426.

33. McKenna C E, Kashemirov B A, Krylov I S, Zakharova V M, inventors; University of Southern California, assignee. Method to Improve Antiviral Activity of Nucleotide Analogue Drugs. Pat. No. 9,550,803. 2017.

34. Krylov I S, Zakharova V M, Serpi M, Haiges R, Kashemirov B A, McKenna C E. Structure of cyclic nucleoside phosphonate ester prodrugs: an inquiry. J Org Chem. 2012. 77(1):684-689. Epub 2011 Dec. 1. doi: 10.1021/jo201735f.

35. McKenna C E, Schmidhuser J. Functional selectivity in phosphonate ester dealkylation with bromotrimethylsi-lane. Journal of the Chemical Society, Chemical Com-munications. 1979. (17):739-739. doi: 10.1039/c39790000739.

36. McKenna C, Higa M, Cheung N, McKenna M. The Facile Dealkylation of Phosphonic Acid Dialkyl Ester by Bromotrimethylsilane. Tetrahedron Lett. 1977. (2):155-158.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the invention and the following claims.

The invention claimed is:

1. A nucleoside phosphonate having formula (3) or (4):

(3)

(4)

B is a purine or pyrimidine base;
X is $CH_2Ph$, $CH_2$, $CH_2CH_2$, or $CHCH_3$;
R is $C(O)R_2$;
$R_1$ is H or alkyl, alkene, ether or thioether; and
$R_2$ is alkyl or alkene.

2. The nucleoside phosphonate of claim 1, wherein B is cytosine or adenine.

3. The nucleoside phosphonate of claim 1, wherein $R_1$ is $C_{12-18}$ alkyl and $R_2$ is alkyl.

4. The nucleoside phosphonate of claim 1, wherein $R_1$ is $C_{12-18}$ alkyl, $(CH_2)_nCH$—$CHC_{n1}$, $(CH_2)_n$—O—$(CH_2)_{n1}$ or $(CH_2)_n$—S—$(CH_2)_{n1}$ wherein n and/or n1 are 4 to 9 and $R_2$ is $C_{8-18}$ alkyl.

5. A pharmaceutical composition comprising at least one compound of claim 1, and a pharmaceutically acceptable carrier.

6. A method of treating a virus infection comprising administering to a subject an effective amount of at least one nucleoside phosphonate of claim 1.

7. The method of claim 6, wherein the virus infection is caused by a virus selected from the group consisting of RNA virus, an DNA virus, a retrovirus, a herpesvirus, an adeno-virus, an emerging virus of pandemic potential, VZV, CMV, HPV, and SARS-COV-2.

8. A method of treating cancer comprising administering to a subject an effective amount of at least one compound of claim 1.

9. A nucleoside phosphonate having formula (3) or (4):

(3)

(4)

wherein:
B is a purine or pyrimidine base;
X is $CH_2$, $CH_2CH_2$, or $CHCH_3$;
R is H or $C(O)R_2$;
$R_1$ is H or alkyl, alkene, ether or thioether; and
$R_2$ is alkyl or alkene.

10. The nucleoside phosphonate of claim 9, wherein B is cytosine or adenine.

11. The nucleoside phosphonate of claim 9, wherein $R_1$ is alkyl, alkene, ether or thioether and $R_2$ is alkyl.

12. The nucleoside phosphonate of claim 9, wherein $R_1$ is $C_{12-18}$ alkyl, $(CH_2)_nCH$—$CHC_{n1}$, $(CH_2)_n$—O—$(CH_2)_{n1}$ or $(CH_2)_n$—S—$(CH_2)_{n1}$ wherein n and/or n1 are 4 to 9 and $R_2$ is $C_{8-18}$ alkyl.

13. A nucleoside phosphonate having formula (1):

wherein:
    Z is a cyclic or acyclic sugar-derived bivalent group;
    X is $CH_2$, $CH_2CH_2$, or $CHCH_3$;
    R is $C(O)R_2$;
    $R_1$ is H or alkyl, alkene, ether or thioether; and
    $R_2$ is alkyl or alkene.

14. A compound selected from the group consisting of:

15. A method of preparing a nucleoside phosphate (NP), comprising conjugation of phosphorylated amino acid with pyrophosphate, as outlined in the following reaction scheme:

-continued wherein B is a purine or pyrimidine base; R is H or C(O)NHR$_2$, wherein R$_2$ is C$_{8-18}$ alkyl; and R$_1$ is NHR$_{1a}$, wherein R$_{1a}$ is H, alkyl, alkene, ether or thioether, and Y is O, NH, CH$_2$, CHF, CHCl, CHBr, CF$_2$, CCl$_2$, CBr$_2$, CCH$_3$, C(CH$_3$)$_2$, CHN$_3$, or CCH$_3$N$_3$.

16. The method of claim 15, wherein B is cytosine, guanine, adenine or thymine.

17. The method of claim 16, wherein R$_{1a}$ is C$_{12-18}$ alkyl, C$_n$CH=CHC$_{n1}$, C$_n$—O—C$_{n1}$ or C$_n$—S—C$_{n1}$, wherein n and/or n1=4-9 and R$_2$ is C$_{8-18}$ alkyl.

\* \* \* \* \*